United States Patent [19]
Yalkowsky

[11] 3,966,962
[45] June 29, 1976

[54] TRIACETIN SOLUTIONS OF PGE-TYPE COMPOUNDS

[75] Inventor: Samuel H. Yalkowsky, Portage, Mich.

[73] Assignee: The Upjohn Company, Kalamazoo, Mich.

[22] Filed: Mar. 27, 1975

[21] Appl. No.: 562,535

[52] U.S. Cl. .............................. 424/305; 424/317
[51] Int. Cl.$^2$ ................ A61K 31/215; A61K 31/19
[58] Field of Search .................... 424/317, 318, 305

[56] References Cited
UNITED STATES PATENTS

| | | | |
|---|---|---|---|
| 3,829,579 | 8/1974 | Stehle et al. ...................... | 424/318 |
| 3,833,725 | 9/1974 | Thompson ......................... | 424/317 |

OTHER PUBLICATIONS
Merck Index – eighth edition (1968) p. 1064.

*Primary Examiner*—Sam Rosen
*Attorney, Agent, or Firm*—Earl C. Spaeth

[57] ABSTRACT

A stable dosage form of PGE-type compounds is obtained by dissolving these compounds in triacetin.

9 Claims, No Drawings

TRIACETIN SOLUTIONS OF PGE-TYPE COMPOUNDS

DESCRIPTION OF THE INVENTION

This invention relates to novel compositions of matter and to methods for using them. More specifically, this invention relates to novel solutions of certain relatively unstable organic compounds useful for a variety of pharmacological and medical purposes. These novel solutions are surprisingly stable on storage compared with other known solutions of these compounds. These novel solutions are also useful as dosage forms of these organic compounds.

Still more specifically, this invention relates to solutions of a group of pharmacologically and medically useful organic compounds known as prostaglandin-like compounds of the PGE-type. The solvent for these solutions is the normally liquid substance known as triacetin. Triacetin is also known as the tri-acetic acid ester of 1,2,3-trihydroxypropane or glycerol, and is also named glyceryl triacetate. For convenience hereinafter, this substance will be referred to as triacetin.

These novel solutions are surprisingly and unexpectedly stable compared with other known solutions of prostaglandin-like compounds of the PGE-type. Moreover, these novel triacetin solutions are surprisingly useful as dosage forms of these compounds, offering in addition to stability in storage, also the advantages of suitability for and ease of pharmaceutical formulation, relative non-toxicity of the vehicle, namely triacetin, and appropriate release of the prostaglandin-like compound after administration of the dosage form to an animal or a human.

Prostaglandins are related in structure to the substance known as prostanoic acid which has the following structural formula and atom numbering:

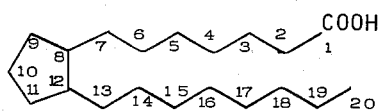

Prostaglandins of the E-type (PGE-type) all have the following structural feature:

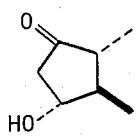

The prostaglandin known as prostaglandin $E_1$ (PGE$_1$) has the formula:

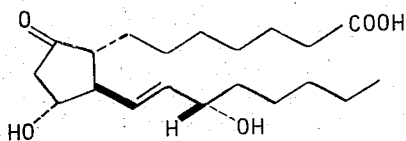

The prostaglandin known as prostaglandin $E_2$ (PGE$_2$) has the formula:

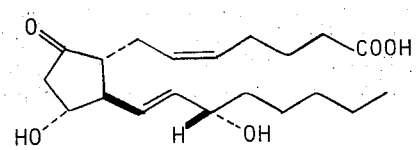

The prostaglandin known as prostaglandin $E_3$ (PGE$_3$) has the formula:

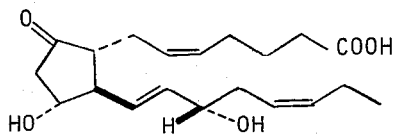

The prostaglandin known as dihydroprostaglandin $E_1$ (dihydro-PGE$_1$) has the formula:

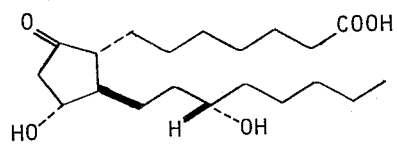

Esters of prostaglandins of the E-type are also known in the art. See, for example, U.S. Pat. Nos. 3,069,322 and 3,598,858.

As is known in the art, prostaglandins of the E-type and their esters are extremely potent in causing various biological responses. For that reason, these compounds are useful for pharmacological and pharmaceutical purposes. See, for example, Bergstrom et al., Pharmacol. Rev. 20, 1 (1968), and references cited therein. A few of those biological responses are systemic blood pressure lowering as measured, for example, in anesthetized (pentobarbital sodium) pentolinium-treated rats with indwelling aortic and right heart cannulas; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion as shown in dogs with secretion stimulated by food or histamine infusion; activity on the central nervous system; controlling spasm and facilitating breathing in asthmatic conditions; and decreasing blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen.

Because of these biological responses, these known prostaglandins of the E-type and their esters are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these E-type prostaglandins are useful in mammals, including man, as nasal decongestants. For this purpose, the compounds are used in a dose range of about 10 μg. to about 10 mg. per ml. of a pharmacologically suitable liquid vehicle or as an aerosol spray, both for typical application.

The E-type prostaglandins are useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly; or by inhalation in the form of aerosols or solutions for nebulizers. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other anti-asthmatic agents, such as sympathomimetics (isoproterenol, phenylephrine, ephedrine, etc.); xanthine derivatives (theophylline and aminophylline); and corticosteroids (ACTH and predinisolone). Regarding use of these compounds see South African Pat. No. 681,055.

The E-type prostaglandins are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 $\mu$g. to about 500 $\mu$g. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The E-type prostaglandins are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. Doses in the range about 0.005 to about 20 mg. per kg. of body weight per day are used, the exact dose depending on the age, weight, and condition of the patient or animal, and on the frequency and route of administration.

The E-type prostaglandins are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, PGE$_2$, for example, is useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the E-type prostaglandin is administered by intravenous infusion immediately after abortion or delivery at a dose in the range about 0.01 to about 50 $\mu$g. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The E-type prostaglandins are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 $\mu$g. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration, especially for PGE$_2$, is oral.

The E-type prostaglandins are useful for controlling the reproductive cycle in ovulating female mammals, including humans and animals such as monkeys, rats, rabbits, dogs, cattle, and the like. By the term ovulating female mammals is meant animals which are mature enough to ovulate but not so old that regular ovulation has ceased. For that purpose, PGE$_2$, for example, is administered systemically at a dose level in the range 0.001 mg. to about 2 mg. per kg. of body weight of the female mammal, advantageously during a span of time starting approximately at the time of ovulation and ending approximately at the time of menses or just prior to menses. Intravaginal and intrauterine are alternative routes of administration. Additionally, expulsion of an embryo or a fetus is accomplished by similar administration of the compound during the first or second third of the normal mammalian gestation period.

The E-type prostaglandins are useful in causing cervical dilation in pregnant and nonpregnant female mammals for purposes of gynecology and obstretrics. In labor induction and in clinical abortion produced by these compounds, cervical dilation produced by PGE-type compounds is useful in assisting sperm movement to the uterus. Cervical dilation by prostaglandins is also useful in operative gynecology such as D and C (Cervical Dilation and Uterine Curettage) where mechanical dilation may cause performation of the uterus, cervical tears, or infections. It is also useful in diagnostic procedures where dilation is necessary for tissue examination. For these purposes, the PGE-type compounds are administered locally or systemically. PGE$_2$, for example, is administered orally or vaginally at doses of about 5 to 59 mg. per treatment of an adult female human, with from one to five treatments per 24 hour period. PGE$_2$ is also administered intramuscularly or subcutaneously at doses of about one to 25 mg. per treatment. The exact dosages for these purposes depend on the age, weight, and condition of the patient or animal.

As mentioned above, the E-type prostaglandins are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

Many prostaglandin-like compounds of the PGE-type are also known in the art. All of these have the same cyclopentane ring structural feature of formula II, above, but differ from the prostaglandins of the E-type in one or more other structural aspects, for example, in having one or more substituents, for example, alkyl, fluoro, phenyl, or cycloalkyl, on either or both side chains, in having fewer or more methylene groups in one or both of the side chains, in having a hetero atom, for example, oxygen in place of a side-chain methylene group, in having cis rather than a trans or a trans rather than a cis configuration for a side-chain carbon-carbon double bond, or in any combination of those structural aspects. With reference to the numbering system of prostanoic acid (formula I above), some examples of E-type prostaglandin-like compounds are 15-methyl-$PGE_1$, 15(R)-15-methyl-$PGE_1$, 15-methyl-$PGE_2$, 15(R)-15-methyl-$PGE_2$, 16,16-dimethyl-$PGE_1$, 16,16-dimethyl-$PGE_2$, 3-oxa-$PGE_1$, 3-oxa-$PGE_2$, 5-oxa-$PGE_2$, 7-oxa-$PGE_1$, 17-phenyl-18,19,20-trinor-$PGE_2$, $PGE_1$ 15-methyl ether, $PGE_2$ 15-methyl ether, 5,6-trans-$PGE_2$, 20-ethyl-$PGE_2$, 20-methyl-$PGE_1$, 16-fluoro-$PGE_2$, 16-phenoxy-17,18,19,20-tetranor-$PGE_2$, and the esters of all of those. As examples of prior art which discloses these E-type prostaglandin-like compounds and others of the E-type, see U.S. Pat. Nos. 3,639,463, 3,759,978, 3,767,695, 3,781,325, 3,804,889, 3,812,179, 3,813,433, 3,833,640, 3,835,180, 3,842,118, 3,847,966, 3,849,487, 3,855,270, and 3,864,387. See also German Offenlegungschrift Nos. 1,937,675, 1,937,921, 2,011,969, 2,036,471, 2,118,686, 2,121,980, 2,144,048, 2,150,361, 2,154,309, 2,165,184, 2,209,990, 2,217,044, 2,221,443, 2,317,019, 2,320,552, 2,322,673, 2,332,400, 2,345,685, 2,423,155, and 2,423,156. See also French Pat. No. 2,119,855, Dutch patent application No. 7,206,316, and Belgian Pat. Nos. 779,898 and 782,822, these being available in printed form through Derwent CPI accession Nos. 76213T-B, 76383T-B, 49033T-B, and 72340T-B, respectively.

The above-described structural variants of the E-type prostaglandins are useful for the same purposes described above for the E-type prostaglandins, and are used for those purposes in the ways described above. Moreover, many of these prostaglandin analogs, for exaple, the 15-methyl, 16,16-dimethyl, 17-phenyl-18,19,20-trinor, and 16-phenoxy-17,18,19,20-tetranor compounds, especially of the $PGE_2$-type, have a longer duration of action in the body than, for example, $PGE_2$ itself, and can be used by routes of administration, for example, oral, for pharmacological or medical purposes for which $PGE_2$, for example, is not desirably effective.

For the purposes of this invention, the term "prostaglandin-like compounds of the E-type" includes both prostaglandins of the E-type, namely $PGE_1$, $PGE_2$, $PGE_3$, dihydro-$PGE_1$, and the esters of those, and also the other carboxylic acids and esters thereof of the type exemplified above, namely those which are structurally similar to the E-type prostaglandins, having a cyclopentane moiety of formula II but with structural variations in either or both side chains, and causing at least part of the biological responses caused by E-type prostaglandins.

Also for the purposes of this invention, the term "prostaglandin-like compounds of the E-type" is intended to include optically active compounds with the same absolute configuration as optically active $PGE_1$ obtained from certain mammalian tissues, for example, sheep vesicular glands or human seminal plasma. See, for example, Bergström et al., J. Biol. Chem. 238, 3555 (1963). This term is also intended to include racemic compounds but not the enantiomers of said optically active compounds. Thus, for example, the compound designated $PGE_2$ means an optically active compound with the natural configuration, and the corresponding racemate, and the compound designated 15-methyl-$PGE_2$ means an optically active compound with the absolute configuration of $PGE_1$, and also the corresponding racemate.

Also for the purposes of this invention, the term "prostaglandin-like compounds of the E-type" is intended to include not only the carboxylic acids but also the esters of said carboxylic acids. Typical esters are those wherein the esterifying radical is alkyl of one to 12 carbon atoms, inclusive, cycloalkyl of 3 to 10 carbon atoms, inclusive, aralkyl of 7 to 12 carbon atoms, inclusive, phenyl, and phenyl substituted with one, 2, or 3 chloro or alkyl of one to 4 carbon atoms, inclusive. Especially useful for the above described purposes are alkyl esters of one to four carbon atoms, inclusive, more especially methyl and ethyl esters.

One problem that has been observed in using and formulating prostaglandin-like compounds of the E-type is the stability of the compounds. These compounds tend to decompose, especially at room temperatures, e.g., about 25° C., and higher, and especially in the presence of small amounts of acid or base. In particular, in the presence of acid, $PGE_2$, for example, changes to $PGA_2$ which has the formula:

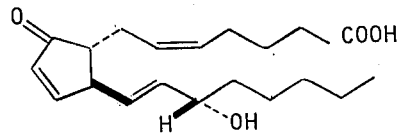

In the presence of base, $PGE_2$ changes to $PGB_2$ which has the formula:

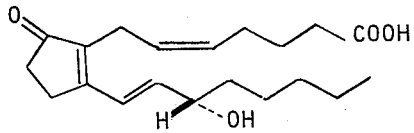

Similarly, the other prostaglandin-like compounds of the E-type change to the corresponding compounds of the A-type or the B-type. Even in neutral aqueous solution or in the solid state, there is a gradual change of E-types to A-types and B-types.

Reasonable stability of prostaglandin-like compounds of the E-type has been observed in some solutions or in solid form when those are maintained at very low temperatures, for example, at −20° C. or lower. However, storage under such temperature conditions is usually inconvenient when the compounds are being used for the above-described purposes. Better success at stabilization has been attained with other solutions and other compositons. See, for example, U.S. Pat. Nos. 3,749,800, 3,826,823, 3,829,579, and 3,851,052. See also Srivastava et al., Lipids 8, 592 (1973) for a study of the possible use of ethyl acetate, chloroform, and ethanol as stabilizing solvents for $PGE_1$, $PGE_2$, and $PGE_3$. But the prior art does not to my knowledge disclose any solution of a PGE-type compound in a solvent which has a useful stabilizing effect on the prostaglandin and wherein said solution is also useful as a dosage form for direct administration to a mammalian animal, including a human, without dilution with water or some aqueous solution. All prior art attempts to produce storage stable forms of PGE-type compounds have resulted in solid compositions which must be dissolved or otherwise dispersed in a pharmaceutical carrier, or in solutions which must be diluted with some pharmaceutical carrier, for example, water, before administration. For example, the use of dimethylacetamide and other solvents mentioned in U.S. Pat. No. 3,829,579 results in solutions which though of useful stability are not suitable as dosage forms, each requiring substantial dilution with water, aqueous solutions, or other pharmaceutical carriers before pharmacological or medical use. Moreover, when these prior art PGE-type solid compositions and solutions are brought into contact with substantial amounts of water or aqueous solution, as must be done before administration by most of the usual routes to animal or human subjects, the result is a solution which undergoes rather rapid decomposition. Although this situation can be tolerated in pharmacological and medical practice, it lacks pharmaceutical elegance, and there is no need to tolerate it if there is an alternative. It is such an alternative that I have invented.

I have now discovered that solutions of PGE-type prostaglandins in the normally liquid substance known as triacetin are unexpectedly stable and are also useful as dosage forms for direct administration of the prostaglandin to animal and human subjects, especially by the oral route.

Triacetin at a NF degree of purity is a colorless, somewhat oily liquid having a slight fatty odor and to some persons a somewhat bitter taste. At least 95% of NF grade triacetin distils between 257° and 260° C., and the NF grade contains no more than about 0.2% water. Triacetin is also included in the GRAS (generally regarded as safe) list of the U.S. Food and Drug Administration. Triacetin is soluble in water to the extent of about one part of triacetin to 14 parts of water. It is the NF grade of triacetin which is preferred for preparation of the novel stable dosage forms of this invention.

Triacetin is a well known article of commerce, being used mainly in various industrial applications. Some pharmaceutical uses of triacetin have, however, been suggested. For example, triacetin has been proposed as the active ingredient in various antifungal compositions. See U.S. Pat. No. 3,070,497 and British specification No. 845,029. A solution of chloroazodin in triacetin is listed in NF X as a topical antiseptic, although this solution has not been listed as official in subsequent editions of the NF (see NF XI). See also U.S. Pat. No. 2,630,399 and U.S. Pat. No. 2,638,434 for topical preparations containing other active chlorine compounds in combination with triacetin. U.S. Pat. No. 3,219,529 discloses the use of a wide assortment of organic substances, including triacetin, as solvents which yield stable solutions of the neutral or amphoteric tetracyclines. According to this patent, these solutions are intended largely as storage forms which are to be diluted with water prior to use as antibiotics. U.S. Pat. No. 3,577,516 discloses the use of a large variety of organic substances, including triacetin, as plasticizer-solvents in the formulation or aerosol packs intended to form a spray-on bandage comprising a water-dispersable polymeric material such as Hydron S. Also, monoacetin, diacetin, and triacetin have been studied as possible stabilizing substances in aqueous solutions of $\alpha$-chymotrypsin. See Matsuoka et al., Yakuzaigaku 25, 59 (1965) (Japan) as abstracted by Chemical Abstracts 65, 18432d (1966).

There is, however, no indication whatever in the above-cited prior art relating to PGE-type prostaglandins and to triacetin which suggests the unexpected stability of triacetin solutions of these prostaglandins and the surprising effectiveness of the solutions as dosage forms for direct administration to animal and human subjects.

As an example of the surprising stability of triacetin solutions of PGE-type compounds, a solution of 16,16-dimethyl-$PGE_2$ in triacetin was prepared to contain about 2 mg. of the prostaglandin per ml. of triacetin. Portions of this solution were maintained at various temperatures, aliquots being analyzed at 4-week intervals. The following data were obtained, the number below each temperature being the concentration of prostaglandin in the solution in mg. per ml.:

| Week | 4°C. | 25°C. | 40°C. | 47°C. | 56°C. | 70°C. |
| --- | --- | --- | --- | --- | --- | --- |
| 4  | 2.25 | 2.20 | 2.18 | 2.08 | 1.82 | 1.77 |
| 8  | 2.21 | 2.15 | 2.09 | 1.98 | 1.82 | 1.53 |
| 12 | 2.15 | 2.14 | 1.93 | 1.83 | 1.90 | 1.44 |
| 16 | 2.21 | 2.06 | 1.95 | 1.86 | *    | *    |
| 20 | 2.20 | 2.15 | 2.06 | 1.95 | *    | *    |
| 24 | 2.23 | 2.10 | 1.93 | 1.83 | *    | *    |
| 28 | 2.25 | 2.18 | 2.18 | 2.06 | *    | *    |

(* analysis discontinued)

These data show that at 4° C. and 25° C. there is no decomposition of the prostaglandin detectable within the experimental errors of the analysis.

In the practice of this invention, it is preferred that the concentration of the PGE-type compound in the triacetin solution be in the range 0.1 to 10 mg. of compound per ml. of triacetin, although for those PGE-type compounds which are highly active for certain pharmacological or medical uses, lower concentrations can be used, the only criterion being that the water content of the particular tissue area of the animal or human body to which the triacetin solution is administered should be sufficient to dissolve the triacetin and thus release the prostaglandin to the body tissues. Even this criterion is not of significance when the triacetin solution is administered, for example by intramuscular injection, with the intent that there be a depot effect, the prostaglandin being released gradually the pool of triacetin within the body tissues. Concentrations of prostaglandin higher than 10 mg. per ml. can also be used, the only criterion being that the solubility of the PGE-type compound in triacetin is not exceeded. An especially preferred range of concentraton, especially when the oral administration route is used, is 0.5 to 5 mg. of prostaglandin per ml. of triacetin.

To prepare the novel stable dosage forms of this invention, the desired amount of the PGE-type compound is merely added to the desired amount of triacetin, and the mixture stirred at about 25° C. until a homogenous solution is obtained.

The novel triacetin solutions of this invention are administered to the animal or human subject by any of the routes known to be useful for administration of PGE-type prostaglandins except that these novel solutions would not ordinarily be used for administration directly into the blood stream, for example by intravenous or intraarterial injection or infusion. Thus, the triacetin solution is injected subcutaneously or intramuscularly. Alternatively, the triacetin solution is incorporated by methods known in the art into a pack capable of generating an aerosol containing small droplets of the triacetin solution for the treatment of the upper respiratory tract, for example, in the treatment of asthma. The triacetin solutions are also administered by syringe or other known appropriate mechanical means into the rectum, the vagina, the ear canal, or the nostrils to cause desired medical results which are known to occur when compounds of the PGE-type are administered to those areas. These triacetin solutions are incorporated into known suppository bases, preferably bases not containing substantial amounts of water, for rectal and vaginal administration of PGE-type compounds.

The novel triacetin solutions of this invention are especially useful as dosage forms to administer PGE-type compounds by the oral route. Although these solutions are sufficiently acceptable in terms of odor and oily nature to be taken directly into the mouth of the animal or human subject, the taste may be too bitter for some subjects. Moreover, the amount of solution to be administered is usually so small that part of the solution and hence part of the prostaglandin may not reach the appropriate location in the alimentary canal. Therefore, for administration of the triacetin solution by the oral route, it is preferred either that the solution be mixed with water or some aqueous medium, for example, fruit juice, just prior to oral administration, or more preferably, that the triacetin solution be encapsulated, using as capsule material any of the usual materials which are water dispersable. The capsules can be micro capsules, prepared by methods known in the art, the desired dose of prostaglandin then being measured by weight or by volume of micro capsules, or the capsules can be the usual larger type wherein one or a small number of capsules is administered.

When the larger size capsule is used, a preferred capsule material is one which comprises gelatin, the resulting capsules being either the so-called hard type or, more preferably, the soft and relatively elastic type. These novel triacetin solutions are well suited to be encapsulated with the machinery and gelatin masses usually used to prepare gelatin capsules. Moreover, triacetin itself has a minimal effect on the gelatin-containing encapsulation material. If in oral administration of triacetin solutions of the PGE-type prostaglandin, it is desired that the solution not be released from the capsule until the capsule has passed through the stomach, any of the usual enteric coating procedures are used.

Triacetin solutions of PGE-type prostaglandins, especially in capsule form, are especially useful for oral administration to induce labor in humans near term. For that purpose, $PGE_2$ is preferred as the prostaglandin, volumes of the solution being used to supply the $PGE_2$ at appropriate known dose levels. Triacetin solutions of PGE-type compounds, especially in capsule form, are also especially useful for reduction of gastric secretion and hence prevention or healing of peptic ulcers in humans. Here, such PGE-type compounds as 16,16-dimethyl-$PGE_2$, 15-methyl-$PGE_2$, or 15(R)-15-methyl-$PGE_2$ or the methyl esters of those are preferred as the prostaglandins.

My invention is illustrated by the following example, which is not to be construed as limiting with regard to PGE-type prostaglandin, concentration, and final dosage form.

EXAMPLE 16,16-Dimethyl-$PGE_2$ is dissolved in triacetin NF to give a solution of concentration 1.0 mg. of the prostaglandin per ml. of triacetin. A gelatin mass is prepared such that each kg. contains 48% gelatin USP, 24.2% glycerin USP, 27.87% purified water USP, 0.172% methylparaben USP, 330 mg. F.D.&C. Yellow No. 5, 500 mg. ethyl vanillin NF, and 250 mg. vanilla enhancer 51.609/A. Using an encapsulation machine, 0.1 ml. portions of the triacetin solution are filled into soft elastic capsules of this gelatin mass. Each capsule contains 100 µg. of 16,16-dimethyl-$PGE_2$.

Samples of capsules prepared by this procedure are stored at 4° C. for 6 weeks. Assay of the 16,16-dimethyl-$PGE_2$ in the capsules then shows a prostaglandin content within 2% of the original content.

These capsules are used in accord with the procedures of U.S. patent application Ser. No. 465,881, filed May 1, 1974, to reduce gastric secretion in humans, administering 2 to 4 of the capsules per day to adult humans.

Following the above procedures, soft elastic gelatin capsules each containing 100 µg. of one of 16,16-dimethyl-$PGE_2$ methyl ester, 15-methyl-$PGE_2$, 15-methyl-$PGE_2$ methyl ester, 15(R)-15-methyl-$PGE_2$, and 15(R)-15-methyl-$PGE_2$ methyl ester in 0.1 ml. of triacetin are also prepared and administered orally to adult human subjects to reduce gastric secretion.

I claim:

1. A stable dosage form of a prostaglandin-like compound of the PGE-type comprising a solution of said compound in triacetin.

2. A stable dosage form according to claim 1 wherein said solution contains said compound in a concentration range 0.1 to 10 mg. per ml. of triacetin.

3. A stable dosage form according to claim 1 wherein said solution is contained in a capsule of a pharmaceutically acceptable water-dispersable material.

4. A stable dosage form according to claim 3 wherein said material contains gelatin and the capsule is soft and elastic.

5. A stable dosage form according to claim 1 wherein said compound is $PGE_2$, $PGE_2$ methyl ester, 16,16-dimethyl-$PGE_2$, 16,16-dimethyl-$PGE_2$ methyl ester, 15-methyl-$PGE_2$, 15-methyl-$PGE_2$ methyl ester, 15(R)-15-methyl-$PGE_2$, or 15(R)-15-methyl-$PGE_2$ methyl ester.

6. A stable dosage form according to claim 5 wherein the triacetin solution is contained in a soft elastic gelatin capsule, and said compound is present in a concentration range 0.1 to 10 mg. per ml. of triacetin.

7. A stable dosage form according to claim 4 wherein the compound is 16,16-dimethyl-$PGE_2$ or 16,16-dimethyl-$PGE_2$ methyl ester, and said compound is present in a concentration range 0.5 to 5 mg. per ml. of triacetin.

8. A stable dosage form according to claim 4 wherein the compound is 15-methyl-$PGE_2$ or 15-methyl-$PGE_2$ methyl ester, and said compound is present in a concentration range 0.5 to 5 mg. per ml. of triacetin.

9. A stable dosage form according to claim 4 wherein the compound is 15(R)-15-methyl-$PGE_2$ or 15(R)-15-methyl-$PGE_2$ methyl ester, and said compound is present in a concentration range 0.5 to 5 mg. per ml. of triacetin.

* * * * *

UNITED STATES PATENT AND TRADEMARK OFFICE
CERTIFICATE OF CORRECTION

PATENT NO. : 3,966,962
DATED : June 29, 1976
INVENTOR(S) : Samuel H. Yalkowsky

It is certified that error appears in the above-identified patent and that said Letters Patent are hereby corrected as shown below:

Column 2, line 64: "for typical application." should read:
    --for topical application.--.
Column 5, line 39: "2,332,400, 2,345,685, 2,423,155," should
    read: --2,332,400, 2,345,695, 2,423,155,--.
Column 5, line 50: "exaple" should read: --example--.
Column 10, line 18: "for 6 weeks" should read: --for 16 weeks--.

Signed and Sealed this

Twenty-seventh Day of December 1977

[SEAL]

Attest:

RUTH C. MASON
Attesting Officer

LUTRELLE F. PARKER
Acting Commissioner of Patents and Trademarks